(12) United States Patent
Yamada (10) Patent No.: US 10,426,326 B2
(45) Date of Patent: Oct. 1, 2019

(54) FIBER OPTIC CORRECTION OF ASTIGMATISM

(71) Applicant: Canon USA Inc., Melville, NY (US)

(72) Inventor: Daisuke Yamada, Cambridge, MA (US)

(73) Assignee: Canon U.S.A, Inc., Melville, NY (US)

( * ) Notice: Subject to any disclaimer, the term of this patent is extended or adjusted under 35 U.S.C. 154(b) by 0 days.

(21) Appl. No.: 15/949,970

(22) Filed: Apr. 10, 2018

(65) Prior Publication Data

US 2018/0303327 A1    Oct. 25, 2018

Related U.S. Application Data (60) Provisional application No. 62/487,196, filed on Apr. 19, 2017.

(51) Int. Cl.

| A61B 1/07 | (2006.01) |
|---|---|
| A61B 5/00 | (2006.01) |
| A61B 1/313 | (2006.01) |
| G02B 6/02 | (2006.01) |
| G02B 6/028 | (2006.01) |
| A61B 1/00 | (2006.01) |
| G02B 6/26 | (2006.01) |

(52) U.S. Cl.
CPC .............. *A61B 1/07* (2013.01); *A61B 1/3137* (2013.01); *A61B 5/0066* (2013.01); *A61B 5/0084* (2013.01); *A61B 1/00135* (2013.01); *G02B 6/028* (2013.01); *G02B 6/02052* (2013.01); *G02B 6/262* (2013.01)

(58) Field of Classification Search
None
See application file for complete search history.

(56) References Cited

U.S. PATENT DOCUMENTS

| 6,564,089 | B2 * | 5/2003 | Izatt ..................... A61B 5/0066 600/478 |
| 6,801,375 | B2 | 10/2004 | Hayashide |

(Continued)

FOREIGN PATENT DOCUMENTS

| JP | H0460608 A | 2/1992 |
| JP | 2007209536 A | 8/2007 |

(Continued)

OTHER PUBLICATIONS

Yu-Kuan Lu, et al., Asymmetric Elliptic-Cone-Shaped Microlens for Efficient Coupling to High-Power Laser Diodes, Optics Express, Feb. 19, 2007, 15(4):1434-1442, Optical Society of America, Washington DC, 2007.

(Continued)

*Primary Examiner* — Michael Stahl
(74) *Attorney, Agent, or Firm* — Canon U.S.A., Inc. IP Division (57) ABSTRACT

An optical probe for use in medical instrumentation where a sheath is covering the optical probe, wherein the optical probe is configured to correct astigmatism by incorporating asymmetric optical powers.

16 Claims, 10 Drawing Sheets

(56) References Cited

U.S. PATENT DOCUMENTS

| | | | |
|---|---|---|---|
| 6,954,296 B2 | 10/2005 | Takakubo | |
| 7,457,044 B2 | 11/2008 | Ohzawa et al. | |
| 7,920,271 B2 * | 4/2011 | Vakoc | A61B 3/1225 356/479 |
| RE43,875 E | 12/2012 | Shishkov et al. | |
| 8,515,221 B2 | 8/2013 | Flanders et al. | |
| 8,582,934 B2 | 11/2013 | Adler et al. | |
| 8,781,287 B2 | 7/2014 | Flanders et al. | |
| 8,971,679 B2 | 3/2015 | Ho et al. | |
| RE45,512 E | 5/2015 | Tearney et al. | |
| 9,036,966 B2 | 5/2015 | Bhagavatula et al. | |
| 2008/0043244 A1 * | 2/2008 | Hatori | G01B 9/02004 356/479 |
| 2014/0275986 A1 * | 9/2014 | Vertikov | A61B 5/061 600/424 |
| 2014/0288417 A1 | 9/2014 | Schmidtlin et al. | |

FOREIGN PATENT DOCUMENTS

| | | |
|---|---|---|
| JP | 2008514383 A | 5/2008 |
| JP | 2012229976 A | 11/2012 |
| JP | 2013524930 A | 6/2013 |

OTHER PUBLICATIONS

Woonggyu Jung, et al., Numerical Analysis of Gradient Index Lens-Based Optical Coherence Tomography Imaging Probes, Journal of Biomedical Optics, Dec. 30, 2010, vol. 15 issue 6, article 066027, pp. 066027-1-066027-10, , SPIE, Bellingham WA, 2010.

Moritex, OvalTran, oval core lensed optical fibers, Internet Archive Wayback Machine, Oct. 6, 2016, <URL:https://web.archive.org/web/20161006232014/http://moritex.com/products/optocom/optical/optical_telecom_components/6-1-1-4.html>.

Tianshi Wang, et al., Numerical Analysis of Astigmatism Correction in Gradient Refractive Index Lens Based Optical Coherence Tomography Catheters, Applied Optics, Jul. 18, 2012, 51(21):5244-5252, OSA, Washington DC, 2012.

SPIE, Gradient Index Lens, Optipedia, Internet Archive Wayback Machine, May 16, 2016, <URL:http://web.archive.org/web/20160516035942/http://spie.org/publications/tt48_55_gradient_index_lens>.

Kazuo Shiraishi, et al., Explicit Formulas for Transmission Characteristics of Graded-Index Oval Core Fibers, Applied Optics, Jan. 20, 2004, pp. 660-664, vol. 43, No. 3, Optical Society of America, Washington DC.

* cited by examiner

FIBER OPTIC CORRECTION OF ASTIGMATISM

CROSS REFERENCE TO RELATED PATENT APPLICATIONS

This application claims priority from U.S. Provisional Patent Application No. 62/487,196 filed on Apr. 19, 2017, in the United States Patent and Trademark Office, the disclosure of which is incorporated herein in its entirety by reference.

FIELD OF THE DISCLOSURE

The present disclosure relates to fiber optic probes, and more specifically to an endoscope employing a fiber optic probe capable of correcting astigmatism.

BACKGROUND OF THE DISCLOSURE

It is often useful and necessary for medical or research reasons to obtain images from within a subject. An endoscope or some other medical probe has the ability to provide images from inside the subject. The subject may be a human patient.

The endoscope may include a fiber probe. One or more optical fibers may be utilized to navigate, deliver light to, and receive light from a sample (such as body, organs, tissues and any other materials). The fiber probe may also include a lens and a mirror assembled at a distal end of the fiber to focus light, collect light, and guide the light.

Endoscopes have been developed so as to gain access to internal organs with minimal evasion of the subject. For example in cardiology, OCT (optical coherence tomography) has been developed to see depth resolved images of blood vessels via a catheter. The catheter, which consists of a sheath, a coil, and a fiber optical probe, is navigated to an area of interest such as a coronary artery. As the beam of light from a fiber optical probe is rotated across a surface of interest, cross-sectional images of the vessels are obtained. In order to acquire three-dimensional data, the optical probe is simultaneously translated longitudinally during the rotation so that images based on a helical scanning pattern are obtained. This helical translation may be performed by pulling the tip of a fiber optic probe back towards a proximal end, while it is simultaneously being rotated, and therefore is referred to as a pullback.

The catheter includes a clear sheath in which light from the fiber optic probe passes. The smaller the diameter of the probe, the stronger the optical power that the clear sheath adds along one axis of the optical system, and the greater the astigmatism of the optical system.

U.S. Pat. Nos. RE43,875 and RE45,512 disclose methods in which the refractive index of a sheath substantially matches the refractive index of the medium outside the sheath and a fluid inside the sheath. However, a problem with this method is the lack of accountability for the viscosity and turbulence due to the fluid inside the sheath, while the probe is being pulled back. U.S. Pat. Nos. RE43,875 and RE45,512 also disclosed adding a prolate spheroidal ball to the end of the endoscope to compensate for the astigmatism of the sheath. U.S. Pat. No. 8,582,934 discloses compensating for the astigmatism of the sheath with a curved reflective cap with two different focal points. However, these systems can be difficult to align, manufacture, and maintain.

SUMMARY

Thus there is a need to address these shortcomings in the industry, and provide an imaging system that overcomes the deficiencies of past systems, and compensates for the astigmatism in the probe.

In one embodiment the optical probe comprises a sheath having a hollow interior for housing a light source and a waveguide for guiding the light through the sheath, where the waveguide has an asymmetric optical power for reducing astigmatism when the light travels through the sheath. In various embodiments, the optical probe may have a second waveguide with an elliptical core.

In other embodiments, the optical probe may further comprise at least one of: a radially symmetric GRIN lens; and a radially symmetric gradient index optical fiber.

In yet another embodiment of the optical probe, a portion of the sheath that light from the second waveguide passes through may be in the shape of a hollow cylinder.

In further embodiments of the optical probe, the first waveguide may be selected from one of: a single mode fiber; a multimode fiber; and a double clad fiber.

In an embodiment, the second waveguide may be a graded index fiber.

In another embodiment of the optical probe, a spacer may be included between the first waveguide and the second waveguide, wherein the spacer is selected form one of: a coreless fiber; fiber taper; and a multimode fiber.

In an embodiment of the optical probe, an asymmetry of the second waveguide may be configured to reduce an asymmetry of a spot size of illumination light from the optical probe exits through the sheath.

In yet a further embodiment, the second waveguide may have an elliptical cladding.

In an embodiment, the second waveguide may have a marking on the outer surface that identifies an orientation of one of a major axis and a minor axis of the elliptical core.

Further embodiments of the optical probe, may comprise an optical component that reflects light from the second waveguide and through the sheath.

In one embodiment of the subject optical probe, light from second waveguide is incident on an interface of the optical component at an angle that is greater than a critical angle for total internal reflection.

Further embodiments may comprise a reflective film on a surface of the optical component such that the light is reflected from the elliptical core of the second waveguide based upon total internal reflection.

In an embodiment, the optical component that reflects light from the second waveguide and through the sheath may be a mirror.

In an embodiment, the waveguide may have asymmetric optical powers and may have a optical power of the sheath along a first axis which has the following relationship:

$$P_{fiber_x} \cong P_{fiber_y} + P_{sheath_y} - P_{fiber_y} \cdot P_{sheath_y} L$$

in which: $P_{fiber_y}$ is a first optical power of the waveguide; $P_{fiber_x}$ is a second optical power of the waveguide orthogonal to the first optical power; $P_{sheath_y}$ is the optical power of the sheath along the first axis; and L is an optical distance between the waveguide and the sheath. In some embodiments, the optical power is a dioptric power.

The subject disclosure further teaches an optical probe for optical coherence tomography comprising a sheath having a cylindrical inner surface through which light passes for imaging, and a light guide surrounded by the inner surface of the sheath, for guiding the light with asymmetric optical power, for reducing astigmatism of the light caused by the cylindrical inner surface.

In an embodiment of the subject optical probe for optical coherence tomography, the probe may be configured to obtain intracoronary images.

The subject disclosure further teaches an optical probe comprising a first waveguide, a second waveguide with asymmetric optical power, as well as a sheath, covering the probe.

In further embodiment, the second waveguide may have asymmetric optical powers and may have a optical power of the sheath along a first axis which has the following relationship:

$$P_{fiber_x} \cong P_{fiber_y} + P_{sheath_y} - P_{fiber_y} P_{sheath_y} L$$

in which: $P_{fiber_y}$ is a first optical power of the second waveguide; $P_{fiber_x}$ is a second optical power of the second waveguide orthogonal to the first optical power; $P_{sheath_y}$ is the optical power of the sheath along the first axis; and $L$ is an optical distance between the second waveguide and the sheath.

BRIEF DESCRIPTION OF THE DRAWINGS

Further objects, features and advantages of the present disclosure will become apparent from the following detailed description when taken in conjunction with the accompanying figures showing illustrative embodiments of the present disclosure.

DETAILED DESCRIPTION OF THE DISCLOSURE

In referring to the description, specific details are set forth in order to provide a thorough understanding of the examples disclosed. In other instances, well-known methods, procedures, components and materials have not been described in detail as not to unnecessarily lengthen the present disclosure. It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description and/or illustration to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated. The term "position" or "positioning" should be understood as including both spatial position and angular orientation.

A significant component of an endoscope is the optical fiber. Optical fibers are fragile and sensitive. In order to prevent the attachment of dust, lipids, and/or other contaminants the optical fiber is covered with a cylindrical sheath and/or tube. Astigmatism is introduced because of the optical characteristics of the cylindrical shape of the sheath and/or tube. The astigmatism causes the working distances and beam sizes in two orthogonal directions to be different.

The present disclosure is directed towards an optical fiber probe for an optical imaging systems in which the astigmatism is eliminated or reduced. This results in better quality images because of the astigmatism correction of the beam.

OCT Optical Imaging

Figure 1:
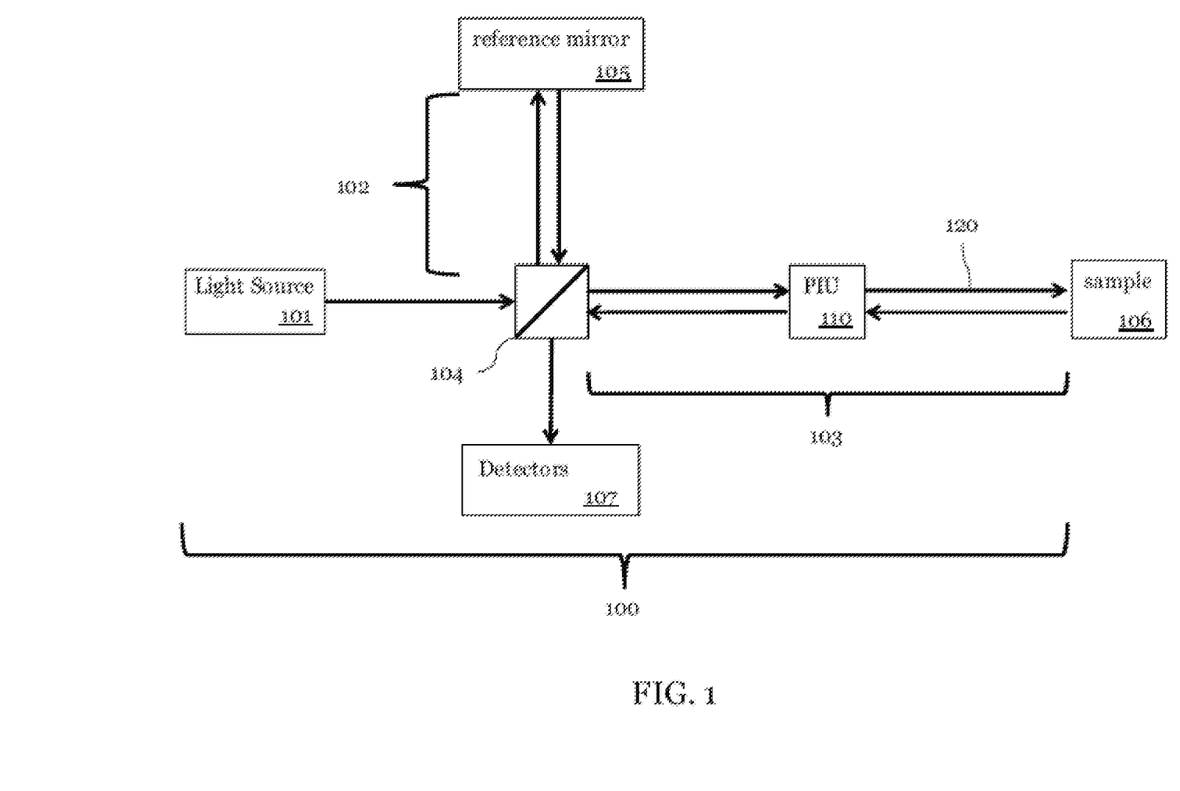
FIG. 1 is an illustration of an optical imaging system incorporating one or more embodiment of the subject disclosure.

FIG. 1 is an illustration of an optical imaging system incorporating one or more embodiment of the subject disclosure. FIG. 1 shows an exemplary system 100 which can utilize the OCT technique. Light from a light source 101 delivers light which is split into a reference arm 102 and a sample arm 103 by a beam splitter 104. A reference beam is reflected from a reference mirror 105 in the reference arm 102 while a sample beam is reflected or scattered from a sample 106 through a patient interface unit (PIU) 110 and a catheter 120 in the sample arm 103. Both beams are recombined at the beam splitter 104 and generate an interference pattern. The output of the interferometer is detected with one or more detectors 107 such as photodiodes, photomultiplier tubes, a linear CCD array, image sensor, CCD array, CMOS array or any type of a sensor system that provides information about the interference pattern. An interference pattern is generated when the path length of the sample arm 103 matches that of the reference arm 102 to within the coherence length of the light source 101. The light source may be a broad band light source with a short coherence length such as a Superluminescent light emitting diode (SLED), a tunable laser, white light source, or other light sources commonly used in OCTs.

Figure 2:
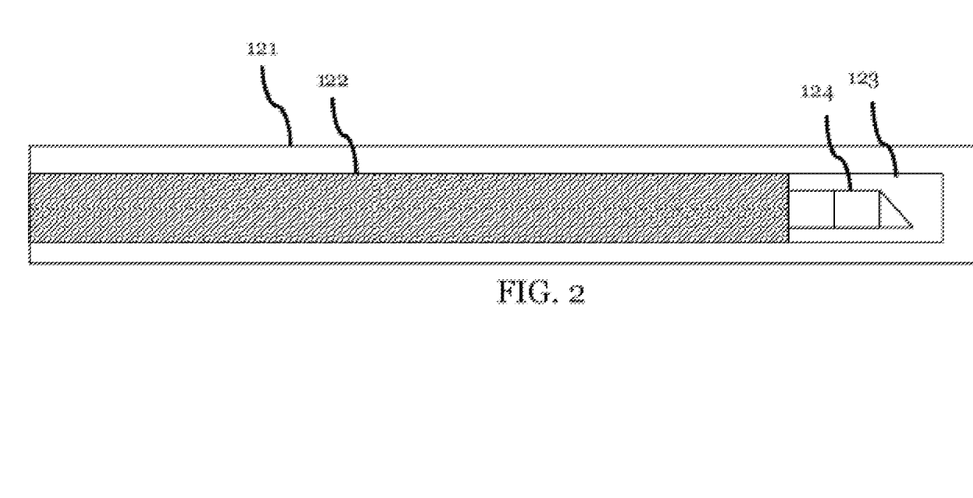
FIG. 2 is an illustration of a catheter incorporating one or more embodiment of the subject disclosure.

FIG. 2 is an illustration of a catheter 120 incorporating one or more embodiment of the subject disclosure. The catheter 120 may consist of a sheath 121, a coil 122, a protector 123, and an optical probe 124. The PIU 110 (not shown) is connected to the coil 122, and rotates the coil 122 during pullback. The coil delivers torque from a proximal end to a distal end of the optical probe 124. The coil 122 is fixed to the optical probe 124 so that a distal tip of the optical probe 124 also rotates. When the distal tip consists of a reflector to reflect light to side through the sheath, an omnidirectional view of an inner surface of a subject such as intracoronary images is provided. The protector 123 may protect the distal tip of the optical probe 124 from damage. The protector 123 may include one or more holes, for allowing light to pass through the one or more holes. The one or more holes may act as apertures and may have other functions. Examples of inners surfaces which may be inspected include hollow organs and vessels, such as the trachea, esophagus, arteries, veins, colon, urinary tract, colon, etc.

First Embodiment of Optical Probe

Figure 3A:
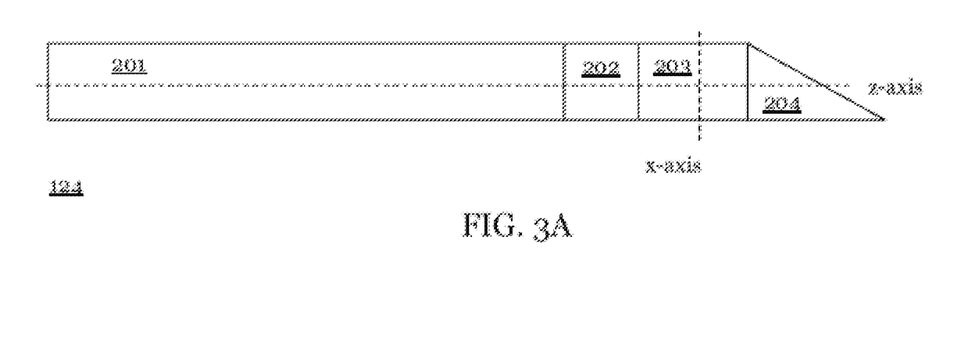
FIGS. 3A-3C are illustrations of an optical probe incorporating one or more embodiment of the subject disclosure.
Figure 3B:
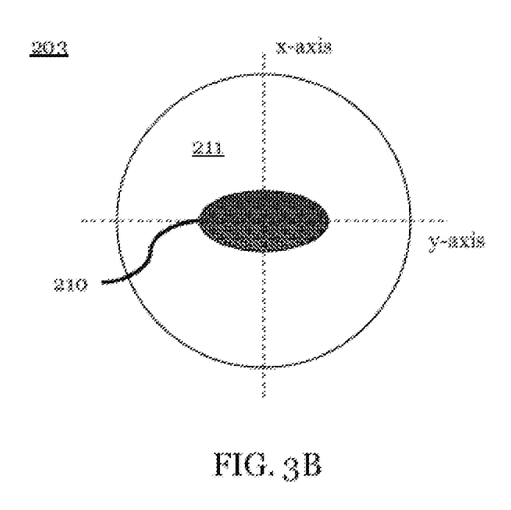
Figure 3C:
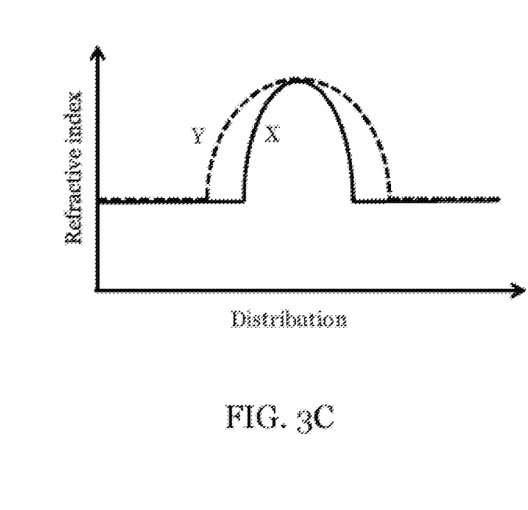

FIGS. 3A-C are illustrations of an optical probe incorporating one or more embodiment of the subject disclosure. FIG. 3A is an illustration of a first embodiment of an optical probe 124. The optical probe 124 may include an optical fiber 201, a glass rod spacer 202, an elliptical core fiber 203, and an angled glass rod spacer 204. The optical fiber 201 is used for delivering the beam of light from the PIU 110. The z-axis illustrated in FIG. 3A is substantially aligned with a central axis of a core of the optical fiber 201. The x-axis is orthogonal to the z-axis. In the context of the present disclosure, substantially aligned means within the measurement and alignment tolerances of the fiber optical system which may be on the micron to sub-micron scale depending on the size of the mode field diameters of the optical components. In one embodiment, the optical fiber 201 may be single mode fiber, multimode fiber, double clad fiber, or triple clad fiber.

The glass rod spacer 202 may be used for adjusting numerical aperture (NA) of the collimating beam. By using glass rod spacers 202 of different lengths, the numerical aperture (NA) may be adjusted. In an alternative embodiment, the optical properties of the glass rod spacer 202 may be adjustable, thus allowing the NA to also be adjustable. In an embodiment, an end face of the glass rod spacer 202 may be fusion spliced to a corresponding end face of the optical fiber 201 thus providing a stable connection between the two components.

FIG. 3B is an illustration of a cross sectional view of the elliptical core fiber 203. The elliptical core fiber 203 is an optical fiber with an elliptic core 210 and an optical cladding 211. The elliptical core fiber 203 is substantially similar to a typical optical fiber, except that a typical optical fiber has a radially symmetric core, while an elliptical core fiber has an elliptical core. The elliptical core fiber may also be a graded index fiber as illustrated in FIG. 3C in which the radial axis varies radially along the both x-axis and the y-axis. As illustrated in FIG. 3C the rate at which the refractive index changes along the y-axis is different from the rate at which the refractive index changes along the x-axis. The graded index profile illustrated in FIG. 3C is a typical smooth profile but other profiles (such as multi-step index) may be used as long as the variation in refractive index provides astigmatic focal power.

The angled glass rod spacer 204 reflects the illumination light through the side of the protector 123 and the sheath 121. Total internal reflection may be used to reflect the illumination light or a mirror surface may be applied to a back surface of the glass rod spacer 204.

In general, the sheath 121 has asymmetric optical power which refracts light from the optical probe due to the cylindrical shape of the sheath 121. The sheath 121 may be employed in a liquid environment such as water, saline, or contrast agents. To compensate for the asymmetric optical power of the sheath 121, another optical component of the system also incorporates an asymmetric optical power. In one embodiment a graded index fiber with an elliptic core can provide asymmetric optical power which compensates for the asymmetric optical power of the sheath 121.

Figure 11:
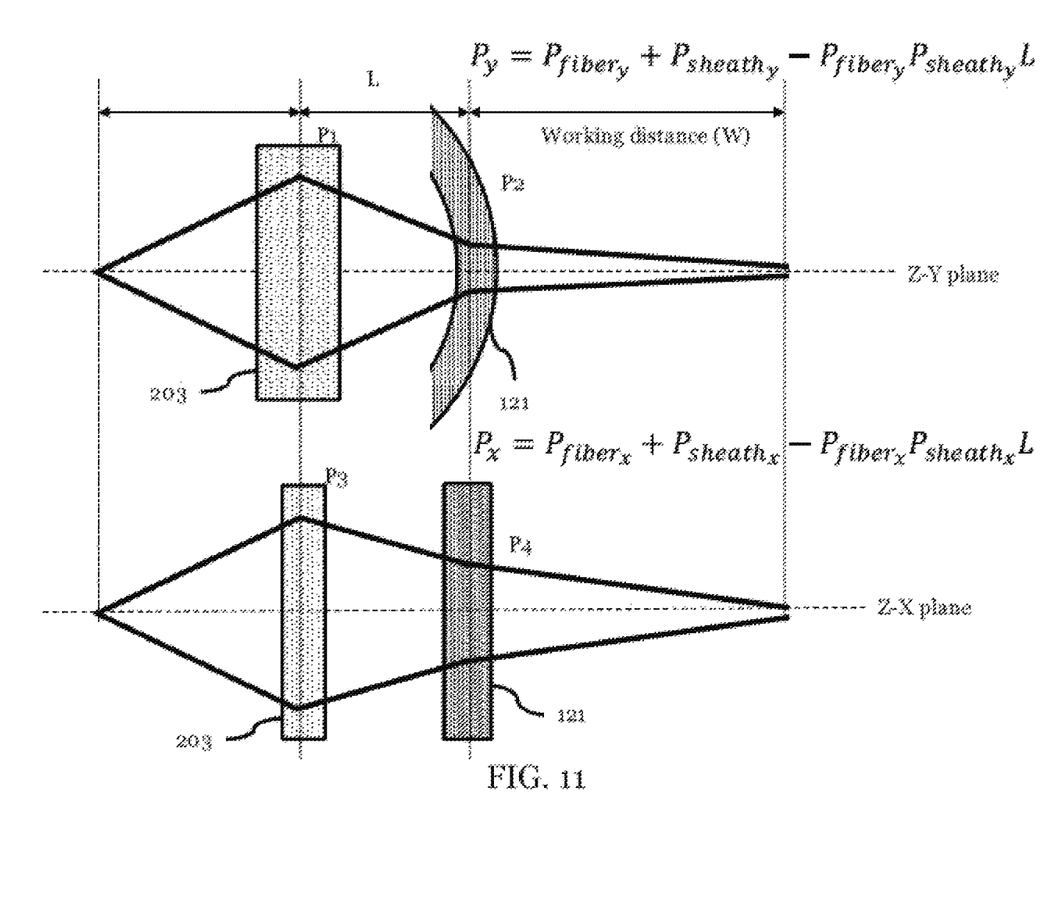
FIG. 11 is a generalized optical schematic of a portion of an imaging system, according to one or more embodiment of the subject disclosure.

FIG. 11 is a generalized optical schematic of a portion of an imaging system, according to one or more embodiment of the subject disclosure. In FIG. 11 the elliptical core fiber 203 and the sheath 121 are visualized along the Z-Y plane and the Z-X plane. The schematic has been simplified to illustrate just the two main elements (203, 121) and their relative asymmetric optical powers P and how they may be used to compensate each other. The graded index elliptical core optical fiber 203 focuses the illumination light at a working distance (W). The combined optical powers of the optical components may be described by equations (1) and (2) below, in which: ($P_y$) is the total optical power along the y axis; ($P_x$) is the total optical power along the x axis; ($P_{fiber_y}$) is the optical power of the elliptical core fiber 203 along the y axis; ($P_{fiber_x}$) is the optical power of the elliptical core fiber 203 along the x axis; ($P_{sheath_y}$) is the optical power of the sheath 121 along the y axis; ($P_{sheath_x}$) is the optical power of the sheath 121 along the x axis; and (L) is an optical distance between the elliptical core fiber 203 and the sheath 121. In which the optical distance (L) is defined by equation (3) in which the area between the elliptical core fiber 203 and the sheath 121 is divided into a plurality of areas each of which has a refractive index ($n_i$) and a distance ($L_i$).

$$P_y = P_{fiber_y} + P_{sheath_y} - P_{fiber_y} P_{sheath_y} L \quad (1)$$

$$P_x = P_{fiber_x} + P_{sheath_x} - P_{fiber_x} P_{sheath_x} L \quad (2)$$

$$L = \sum_{i=j}^{k} L_i n_i \quad (3)$$

In an embodiment, $P_{sheath_x}$ may be approximated with zero. The system may be optimized such that $P_y \cong P_x$, which gives us equation (4):

$$P_{fiber_x} \cong P_{fiber_y} + P_{sheath_y} - P_{fiber_y} P_{sheath_y} L \quad (4)$$

The optical power ($P_{sheath_y}$) of the sheath in the y direction may be described by equation (5) below, in which: (R) is the inner radius; ($\Delta R$) is thickness of the sheath 121; ($n_{sheath}$) is the refractive index of sheath 121; and ($n_{environment}$) is the refractive index outside of the sheath in the environment in which the catheter is deployed.

$$P_{sheath_y} \cong -\frac{n_{sheath} - 1}{R} - \frac{n_{environment} - n_{sheath}}{R + \Delta R} \quad (5)$$

Figure 4:
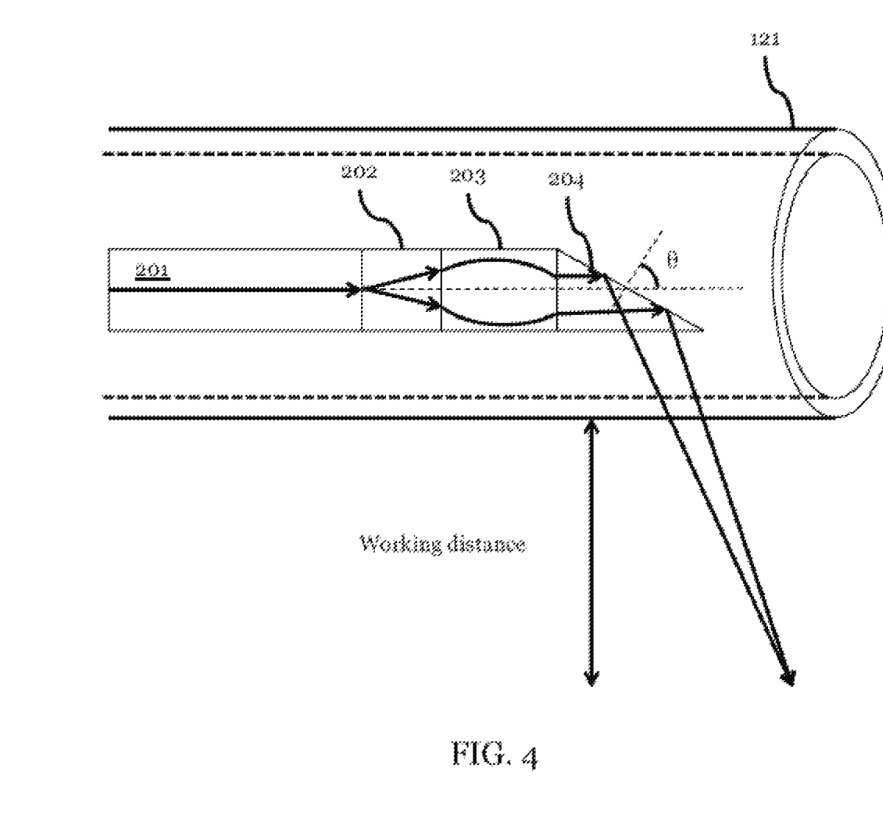
FIG. 4 is an illustration of light exiting a probe, according to one or more embodiment of the subject disclosure.
Figure 5A:
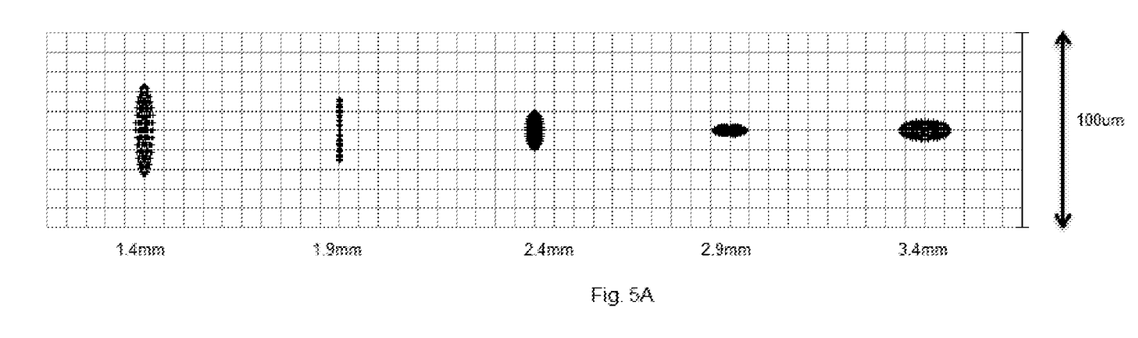
FIGS. 5A-5B are spot diagrams of illumination light, according to one or more embodiment of the subject disclosure.
Figure 5B:
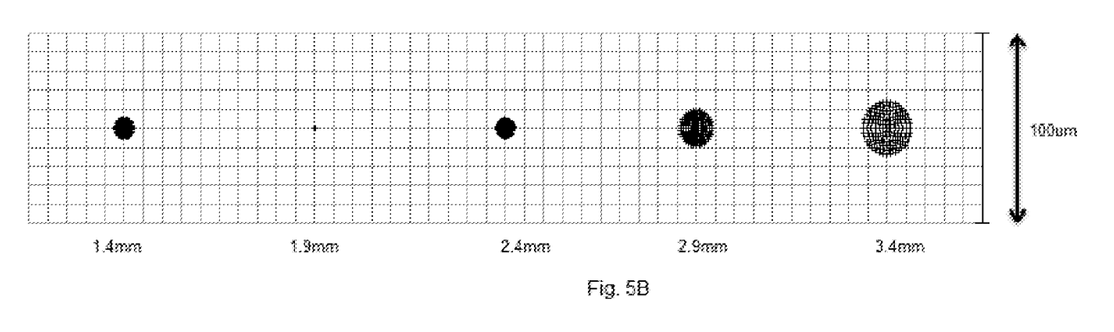

Astigmatism correction is described with FIG. 4 and FIG. 5 as an example.

FIG. 4 is an illustration of light exiting a probe, according to one or more embodiment of the subject disclosure, wherein a light beam with a center wavelength of 1.3 µm is delivered from a light source 101 through an optical fiber 201 made with Corning™ SMF-28e+. After exiting the optical fiber 201, the light diverges through a glass rod spacer 202, which may be made of fused silica and may have a diameter of 125 µm which matches the outer diameter of the SMF-28e+. The length along the z-axis of the glass rod spacer 202 may be around 100 µm.

After the optical beam has been diverged in the spacer 202, the optical beam is converged by the elliptical core fiber 203. The outer diameter of the elliptical core fiber may be 125 µm matching the outer diameter of the spacer 202. The length of the elliptical core fiber 203 along the z-direction may be 950 µm. The elliptical core fiber 203 used in an embodiment has different optical powers ($P_x$, $P_y$) along different axes. The difference in optical power in the two orthogonal directions may be due to there being different refractive index profiles along the x-axis and the y-axis. The length of the elliptical core fiber 203 is chosen to set the asymmetric optical powers ($P_x$, $P_y$) meet the condition described by equation (4) above. For example, elliptical core fibers 203 with an elliptical core 211 are described in a datasheet for the Morixtex Ovaltran™ fiber product number OCT1310D. Elliptical core fibers 203 were also described in Kazuo SHIRAISHI, Akira OGURA, Hidehiko YODA, Explicit Formulas for Transmission Characteristics of Graded-Index Oval Core Fibers, Applied Optics, January 202, 2004, 43(3)660, Optical Society of America, Washington D.C., 2004.

The converged beams exiting the elliptical core 210 may be reflected at the angled surface of the angled glass rod spacer 204. The length of the angled glass rod spacer 204 in the z-direction from a center of the elliptical core fiber 203 to where the z-axis intersects the angled surface may be on the order of 200 µm. The angle θ of the angled surface with the z-axis may be on the order of 50°. The angle range of 30°-60° may be suitable to see side views. Thus, the angle θ is also the angle between incident beam as it exits the elliptical fiber and the angled surface of the angled glass rod spacer 204.

As the beams exit the glass rod spacer 204 they then pass through a cylinder shaped sheath 121. In an embodiment, the sheath 121 may have an inner diameter of 500 µm and an outer diameter of 600 µm. The sheath 121 may have a refractive index of 1.38. Optically, the sheath 121 has negative optical power along a first axis and zero optical power along a second axis orthogonal to the first axis. In an embodiment contrast agents with a refractive index of 1.45 maybe flushed along the outside of the sheath 202 The combination of the elliptical core fiber 203 and the sheath 121 causes the beams to focus at working distance of 1.9 mm (2.5 mm from the z-axis along the center of the probe 124)

A general model for describing radial index profile (n) of a symmetric graded index lens is described by equation (6-1) below. In which $n_0$ is the peak refractive index at the center of the fiber and k is the shape factor. Equation (6-2) is an illustration of how equation (6-1) may be applied to the core 210 of a graded index fiber with a central symmetric refractive index (n) distribution in which (r) is the radius of the core 210. The radius of the core 210 may be 50 µm or 62.5 µm or some other radius.

$$n = n_0\left(1 - \frac{k}{2}(x^2 + y^2)\right) \quad (6\text{-}1)$$

$$n = 1.467\left(1 - \frac{2.743}{2}(x^2 + y^2)\right), x^2 + y^2 < r^2 \quad (6\text{-}2)$$

$$n = 1.467\left(1 - \frac{2.743}{2}r^2\right), x^2 + y^2 \geq r^2$$

The optical power ($P_{fiber}$) of the symmetric graded index fiber has an inverse relationship with the focal length which has a relationship to parameters of as described by equation (6-3) below in which (t) is the length of the fiber. The choice of $t\sqrt{k}$ determines the pitch of the optical fiber if the optical fiber is treated as a GRIN lens.

$$P_{fiber} = \frac{1}{f} = -n_0\sqrt{k}\sin(t\sqrt{k}) \quad (6\text{-}3)$$

In which case the beam in the direction along the y-axis is focused at a working distance of 1.9 mm from the z-axis. However, the beam in the direction along the x-axis is focused at working distance of around 3.4 mm from the z-axis due the sheath 121 as illustrated in FIG. 5A. The astigmatism of the sheath 121 causes the beams to not focus in the x-axis direction at the same position as the y-axis direction. This makes it difficult to minimize the spot size. FIG. 5A is an illustration of the spot size of illumination light after it has passed through the cylindrical sheath 121 at various working distances (1.4 mm, 1.9 mm, 2.4 mm, 2.9 mm and 3.4 mm).

The applicant has found several ways to address this, which makes use of an elliptical core fiber which has a refractive index profile such as the one illustrated in equation (7) below:

$$n = 1.467 - 2.139x^2 - 2.012y^2, x^2 + \frac{2.012}{2.139}y^2 < r^2 \quad (7)$$

$$n = 1.467 - 2.139r^2, x^2 + \frac{2.012}{2.139}y^2 \geq r^2$$

As equation (6-1) was adapted to a symmetric fiber in equation (6-2) above it may also be adapted to an asymmetric fiber described in equation (7) as described in equations (8-1) and (8-2) below. The shape factors $k_x$ and $k_y$ describe the relative shapes of the refractive index profile along the x axis and the y axis. The relative values of $k_x$ and $k_y$ are also related to the shape of the elliptical core as described by the limits in equation (8-2).

$$n = n_0\left(1 - \frac{k_x}{2}x^2 + \frac{k_y}{2}y^2\right) \quad (8\text{-}1)$$

$$n = 1.467\left(1 - \frac{2.916}{2}x^2 + \frac{2.743}{2}y^2\right), x^2 + \frac{2.012}{2.139}y^2 < r^2 \quad (8\text{-}2)$$

$$n = 1.467\left(1 - \frac{2.916}{2}r^2\right), x^2 + \frac{2.012}{2.139}y^2 \geq r^2$$

Equation (6-3) describes optical power of a symmetric graded index fiber while equations (8-3) may be used to describe different optical powers for an asymmetric graded index fiber.

$$P_{fiber_x} = -n_0\sqrt{k_x}\sin(t\sqrt{k_x})$$

$$P_{fiber_y} = -n_0\sqrt{k_y}\sin(t\sqrt{k_y}) \qquad (8\text{-}3)$$

Equation (8-3) may be combined with equations (4)-(5) to describe the relationship between parameters of the sheath and parameters of the elliptical fiber.

$$n_0\sqrt{k_x}\sin(t\sqrt{k_x}) \cong \qquad (8\text{-}3)$$

$$n_0\sqrt{k_y}\sin(t\sqrt{k_y}) + \frac{n_{sheath}-1}{R} - \frac{n_{environment}-n_{sheath}}{R+\Delta R} +$$

$$n_0\sqrt{k_y}\sin(t\sqrt{k_y})\left(\frac{n_{sheath}-1}{R} + \frac{n_{environment}-n_{sheath}}{R+\Delta R}\right)L$$

Equation (8-3) is an example of how asymmetric parameters of an asymmetric optical fiber may be determined based on the asymmetric geometry of the sheath which can then be used to compensate for the astigmatism introduced by the sheath. Other components different asymmetric parameters may be used in the same manner to compensate for astigmatism.

In which case the beams in direction along both the x-axis and y-axis are focused at a working distance of 1.9 mm so that a small spot size may be achieved, as shown in FIG. 5B. FIG. 5B is an illustration of the spot size of illumination light after it has passed through the cylindrical sheath at various working distances (1.4 mm, 1.9 mm, 2.4 mm, 2.9 mm and 3.4 mm) when an elliptical core fiber is used to compensate for the asymmetric distortion of the sheath 121. A comparison of FIGS. 5A and 5B show that the use of the elliptical core fiber allows an embodiment to produce spot sizes with higher radial symmetry relative to the spot sizes produced with a symmetric GRIN lens.

Various embodiment of the subject disclosure may be used with or without the contrast agents. Other embodiment may be used in an air environment or a liquid environment. Liquids which might be used include liquids saline, dextran, water and so on. Further embodiments may make use of different elliptical core fibers 203 depending on the refractive index of the environment in which the catheter 120 is being used. An alternative embodiment may make use of different sheaths 121 depending on the refractive index of the environment in which the catheter 120 is used.

The incidence angle θ of the angled glass rod spacer 204 may be designed to have an incidence angle θ which is greater than the critical angle for total internal reflection. For example, the incidence angle θ may be 50° thus allowing an embodiment to obtain 100% reflection due to total internal reflection on the angled surface and to minimize specular back-reflection from the sheath 121 and/or sample. In an alternative embodiment, angled glass rod spacer 204 may have a mirrored surface. Here, the angled glass rod spacer 204 may be made of fused silica, so that the critical angle for total internal reflection is 43.6°. The glass rod spacer 202 may be used for adjusting both the NA and working distance. In this embodiment, having the elliptical core fiber in distal optics of the catheter, the distal optics provides asymmetric optical powers that correct astigmatism aberrations that are generated in the sheath of the catheter. The beam from the catheter is non- or less astigmatism so that images with high resolution are obtained with the catheter.

Fabrication

Figure 6A:
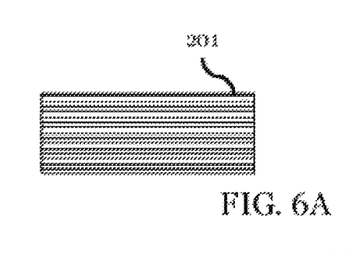
FIGS. 6A-6F are illustrations of various stages of fabricated for a probe, according to one or more embodiment of the subject disclosure.
Figure 6B:
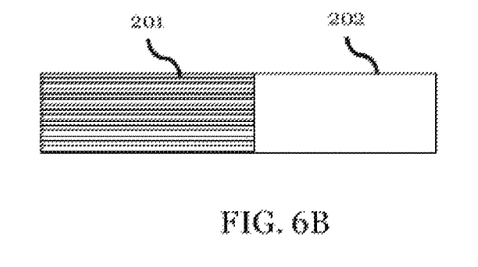
Figure 6C:
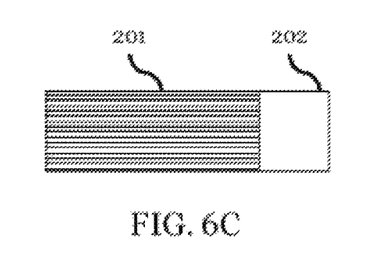
Figure 6D:
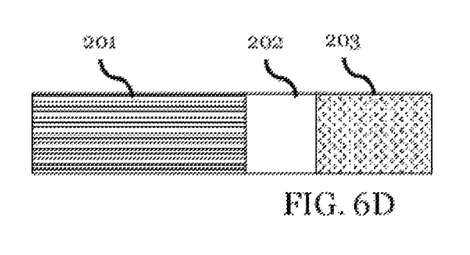
Figure 6E:
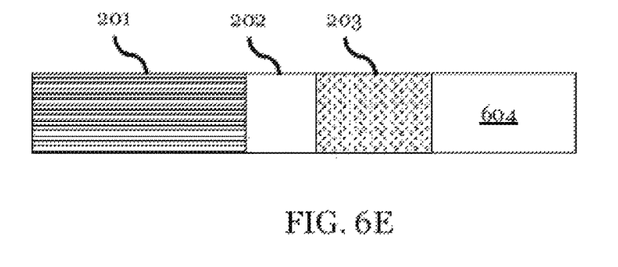
Figure 6F:
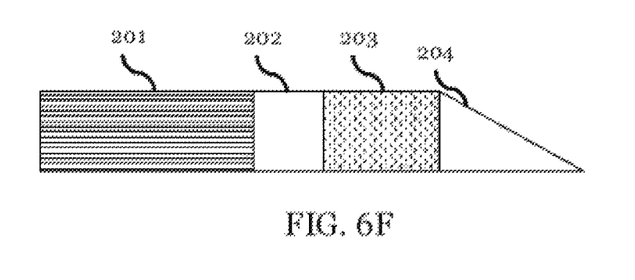

Fabricating the endoscope may include removing a portion of a buffer from an optical fiber 201. The optical fiber 201 may then be cleaved to the desired length as shown in FIG. 6A. Then, the optical fiber 201 may be spliced using a fusion splicer or a mechanical splice to a glass rod spacer 202 as shown in FIG. 6B. The glass rod spacer 202 may then be cleaved to the desired length/position as shown in FIG. 6C. An end face of the glass rod spacer may be polished to obtain an accurate length of the glass rod spacer 202. The elliptical core fiber 203 may be spliced using a fusion splicer or a mechanical splice to the glass rod spacer 202 as illustrated in FIG. 6D. The elliptical core fiber 203 may also be polished. A glass rod 604 may then be attached to the elliptical core fiber 203 this may be done using a fusion splicer or a mechanical splice. The new glass rod 604 may then be polished by 50° to produce the angled glass rod spacer 204 as illustrated in FIG. 6F. In an alternative embodiment, the angled glass rod spacer 204 may be attached directly to the elliptical fiber 203. The direction of the angle of the angled glass rod spacer 204 is aligned with the beam profile Elliptical core fiber 203.

Orientation of the Elliptical Core Fiber

Figure 7A:
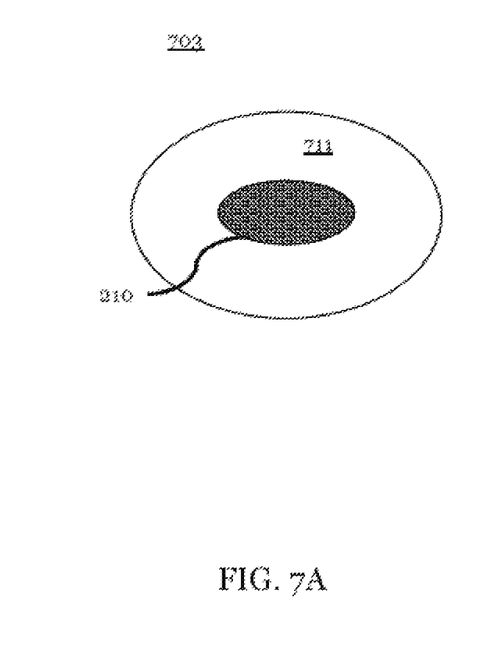
FIGS. 7A-7B are illustrations of portions of an imaging system, according to one or more embodiment of the subject disclosure.
Figure 7B:
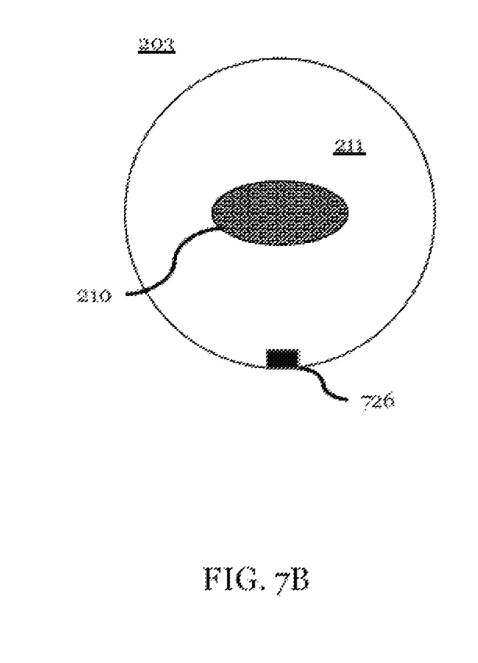

FIGS. 7A-B are illustrations of portions of an imaging system, according to one or more embodiment of the subject disclosure, showing the cross sections of the elliptical core fibers 203 and 703. FIG. 7A is an illustration of an elliptical core optical fiber 703 with both an elliptical core 210 and an elliptical cladding 711. FIG. 7B is an illustration of elliptical core fiber 203 substantially similar to the fiber illustrated in FIG. 3B but also includes a marking 726. The marking 726 is aligned along one of the primary or secondary axes of the elliptical core. The marking 726 may be aligned along a specific axes or may have a specific offset to one of the primary or secondary axes of the elliptical core 703. The marking 726 allows for the alignment of the elliptical core fiber 203 and the polished angled glass rod spacer 204 with appearances without observation of beam profile. The use of an elliptical core fiber 703 with an elliptical cladding 711 may allow for easier mechanical alignment of the angular orientation of the elliptical core 210. While the use of an elliptical core fiber 703 with a radially symmetric cladding 211 allows for easier mechanical alignment of the center of the core 211 of the elliptical fiber with a center of the waveguide 201. A polarization maintaining fusion splicer may be used to set the angular orientation of the elliptical core fiber 703.

Epoxy and/or wax may be used to attach each of the optical components using a mechanical splicing technique instead of a fusion splicing technique. Molded epoxy components may be used in place of the glass rod spacer 202 and/or the angled glass rod 204. Using epoxy and/or wax in the fabrication process allows for lower production costs and may be used for particular wavelength ranges. The fabrication method may include placing the elliptical core fiber and the optical fiber into a mold. The mold including empty volumes for the spacer 202 and an angled spacer 204. One or more different types of epoxy, wax, or other material may be put into the empty volumes. The material in the empty volumes may then be cured via UV, heat, etc. Thus forming the spacer 202 and the angled spacer 204 of an alternative optical material.

The fabrication process above can be applied to other kinds of fibers such as single mode fiber, multi-mode fiber, double clad fiber, photonic crystal fiber, polarization maintaining fiber, glass rod fiber (coreless fiber), plastic fiber. An embodiment may use single fibers, multiple fibers, fiber ribbons, or fiber bundles. In this embodiment, elliptical fiber is used to correct astigmatism aberration. An asymmetric GRIN lens is also used to correct astigmatism aberration. Typically, the refractive index of the GRIN lens is higher than that of fiber materials so that the GRIN lens is able to have high asymmetric optical powers.

Second Embodiment of the Optical Probe

Figure 8A:
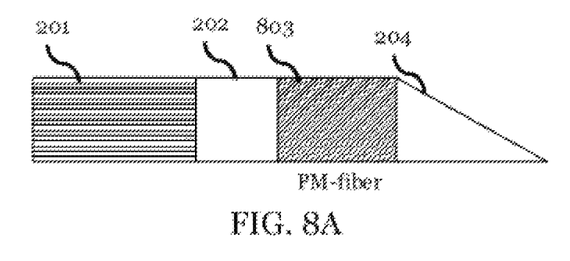
FIGS. 8A-8C are illustrations of portions of an imaging system, according to one or more embodiment of the subject disclosure.

FIGS. 8A-C are illustrations of portions of an imaging system, according to one or more embodiment of the subject disclosure. FIG. 8A is an illustration of a second embodiment of the subject disclosure, in which the elliptical core fiber is replaced with polarization maintaining fiber 803. Examples of a polarization maintaining fiber 803 that may be used are panda-fiber, bow-tie fiber or any fiber that has optical power along a first axis that is different from the optical power along a second axes. Polarization maintaining fiber includes some method of applying stress to the core of the fiber which typically causes the polarization fiber to have any asymmetric index profile. This allows the polarization maintaining fiber to also be used as an asymmetric gradient index lens such as the elliptical core fiber above. The subject disclosure has determined that a short section of the polarization maintaining fiber behaves like a GRIN lens with a pitch that is a function of its length.

Third Embodiment of the Optical Probe

Figure 8B:
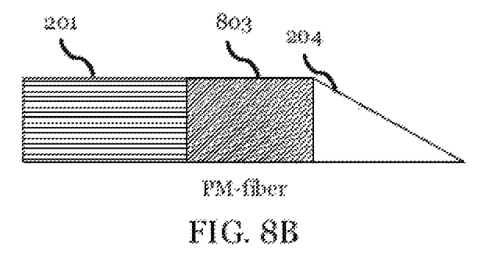

FIG. 8B is substantially similar to the second embodiment except that the spacer 202 is removed. In which case the PM fiber 803 is directly coupled to the optical fiber 201 either via a fusion splice or a mechanical splice.

Fourth Embodiment of the Optical Probe

Figure 8C:
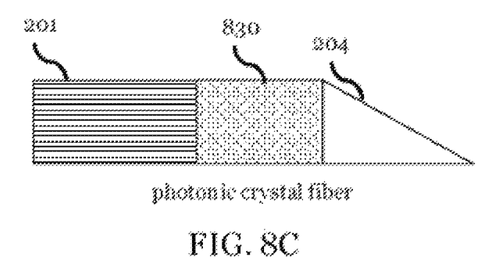

FIG. 8C is substantially similar to the third embodiment except that the PM fiber 803 is replaced with a photonic crystal fiber 830. In this embodiment, the photonic crystal fiber 830 is designed to have asymmetric optical power. The photonic crystal fiber 830 may have an asymmetric solid or air core to achieve the asymmetric optical power. A photonic crystal fiber 830 may be designed to have a custom refractive index distribution so that photonic crystal fiber 830 has a specified asymmetric optical powers using well known methods.

Fifth Embodiment of the Optical Probe

Figure 9A:
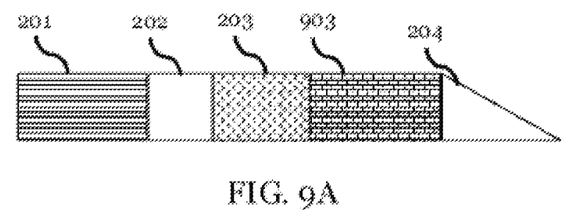
FIGS. 9A-9B are illustrations of portions of an imaging system, according to one or more embodiment of the subject disclosure.
Figure 9B:
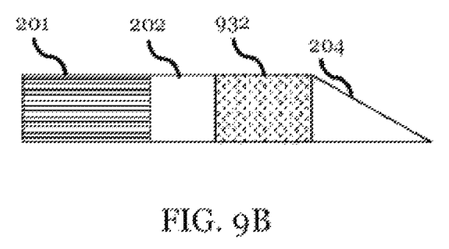

FIGS. 9A-B are illustrations of portions of an imaging system, according to one or more embodiment of the subject disclosure. FIG. 9A is substantially similar to the first embodiment but for the addition of a second GRIN lens 903. This embodiment may include an optical fiber 201 connected to a glass rod spacer 202. The glass rod spacer 202 may be connected to an elliptical core fiber 203. The elliptical core fiber 203 may be connected to a radially symmetric GRIN lens 903. The elliptical core fiber 203 may compensate for the asymmetry of the sheath 121. While the numerical aperture (NA) and working distance may be controlled by the radially symmetric GRIN lens 903. An alternative embodiment may include an additional glass rod space between the elliptical core fiber 203 and the radially symmetric GRIN lens 903. A further embodiment may swap positions of the elliptical core fiber 203 and the radially symmetric GRIN lens 903. The radially symmetric GRIN lens 903 may be gradient index optical fiber. FIG. 9B is an optical probe with a birefringence material 932 such as polymers. The birefringence material 932 introduces different optical powers in two orthogonal directions. Anamorphic optical powers are achieved to combine the birefringence material 932 and standard symmetric lens such as GRIN, GI-fiber, and ball lens. Accordingly, the stigmatism introduced by the cylindrical sheath is corrected with the birefringence materials.

Sixth Embodiment of the Optical Probe

Figure 10A:
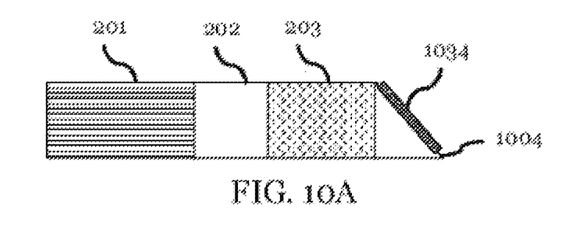
FIGS. 10A-10D are illustrations of portions of an imaging system, according to one or more embodiment of the subject disclosure.

FIG. 10A is another embodiment that is substantially similar to the first embodiment except a reflective coating 1034 is applied to a second angled glass rod spacer 1004 in place of a TIR. In this embodiment, the optical fiber 201 may be connected to the glass rod spacer 202. The glass rod spacer 202 may be connected to the elliptical core fiber 203 or some other component which provides asymmetric focusing power. The elliptical core 203 may be connected to the second angled glass rod spacer 1004 with a reflective coating. The second angled glass rod spacer 1004 may be coated with one or more of a gold coating, aluminum coating, silver coating, other metallic coating, or one or more dielectric layers to achieve high reflectivity. The reflective coating 1034 may improve production yield ratios because it decreases the sensitivity to dust or surface flatness of the angled surface of the angled glass rod spacer 204. In addition, the incidence angle may be made smaller than the critical angle. The second angled glass rod spacer 1004 may be a coreless fiber that has been fusion spliced to the elliptical core fiber 203 and angle cleaved.

Seventh Embodiment of the Optical Probe

Figure 10B:
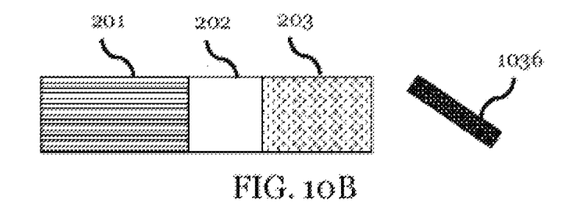

FIG. 10B is a seventh embodiment that is substantially similar to the sixth embodiment except instead of using a reflective coating on a glass rod spacer a mirror 1036 is used. The mirror 1036 is separated from the optical probe. The optical fiber 201 may be connected to the glass rod spacer 202. The glass rod spacer 202 may be connected to the elliptical core fiber 203 or some other component which provides asymmetric focusing power. The rotational orientation of the elliptical core fiber 203 the orientation of the mirror 1036 may be aligned to correct asymmetric focusing power caused by the sheath 121. The distance between the mirror 1036 and an end face of the elliptical core fiber 203 may be adjusted to change the working distance.

Eighth Embodiment of the Optical Probe

Figure 10C:
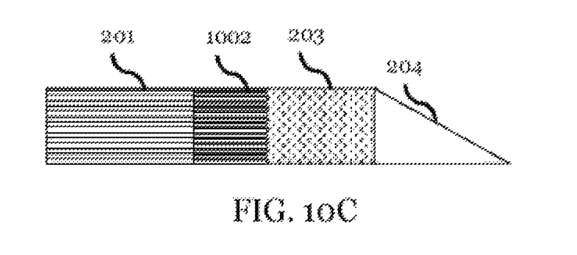

FIG. 10C is an illustration of an eighth embodiment that is substantially similar to the first embodiment except that the coreless fiber 202 is replaced with a multi-mode fiber 1002. In the eighth embodiment, the optical fiber 201 may be connected to a multi-mode fiber 1002. The multi-mode fiber 1002 may be connected to the elliptical core fiber 203 or some other component which provides asymmetric focusing power. The elliptical core fiber 203 may be connected to the angled glass rod spacer 204. In an embodiment, the optical fiber 201 is a double clad fiber, in which the core is used to deliver illumination light, and the inner cladding is used to guide received light.

Ninth Embodiment of the Optical Probe

Figure 10D:
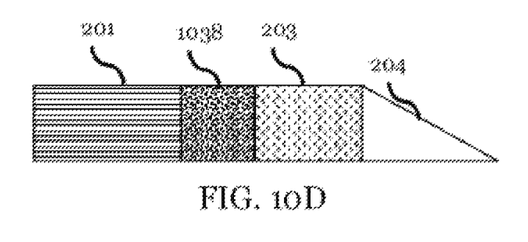

FIG. 10D is an illustration of a ninth embodiment that is substantially similar to the first embodiment except that the coreless fiber 202 is replaced with a fiber taper 1038. In the ninth embodiment, the optical fiber 201 may be connected to a fiber taper 1038. The fiber taper 1038 may be connected to the elliptical core fiber 203 or some other component which provides asymmetric focusing power. The elliptical core fiber 203 may be connected to the angled glass rod spacer 204. The fiber taper 1038 has a core with a tapered structure. On a first end of the fiber taper 1038, the mode field diameter substantially matches the mode field diameter of the optical fiber 201. In the context of the present embodiment, substantially matching mode field diameters mean that the difference between the two mode field diameters is less than 2 microns. On a second end of the fiber taper 1038, the mode field diameter substantially matches the mode field diameter of the elliptical core fiber 203. The elliptical core fiber 203 has a major mode field diameter and minor mode field diameter. In an embodiment, on the second end of the fiber taper 1038, the mode field diameter substantially matches one of the major mode field diameter; the minor mode field diameter or an average of the major and minor mode field diameters of the elliptical core fiber 203.

While the present disclosure has been described with reference to exemplary embodiments, it is to be understood that the disclosure is not limited to the disclosed exemplary embodiments. The scope of the following claims is to be accorded the broadest interpretation so as to encompass all modifications, equivalent structures, and functions.

The invention claimed is:

1. An optical probe comprising:
    a sheath having a hollow interior for housing a light source; and
    a waveguide for guiding a light created by the light source through the sheath,
    wherein the waveguide has asymmetric optical power for reducing astigmatism of the light traveling through the sheath.

2. The optical probe according to claim 1, further comprising a second waveguide with an elliptical core.

3. The optical probe according to claim 1, further comprising at least one of: a radially symmetric GRIN lens; and a radially symmetric gradient index optical fiber.

4. The optical probe according to claim 1, wherein the waveguide is selected from one of: a single mode fiber; a multimode fiber; a double clad fiber; and a triple clad fiber.

5. The optical probe according to claim 2, wherein the second waveguide is a graded index fiber.

6. The optical probe according to claim 2, further comprising a spacer between the waveguide and the second waveguide, wherein the spacer is selected from one of: a coreless fiber; fiber taper; and a multimode fiber.

7. The optical probe according to claim 2, wherein an asymmetry of the second waveguide is configured to reduce an asymmetry of a spot size of illumination light from the optical probe traveling through the sheath.

8. The optical probe according to claim 2, wherein the second waveguide has an elliptical cladding.

9. The optical probe according to claim 2, wherein the second waveguide has a marking on the outer surface that identifies an orientation of one of a major axis and a minor axis of the elliptical core.

10. The optical probe according to claim 2, further comprising an optical component that reflects light from the waveguide or second waveguide and through the sheath.

11. The optical probe according to claim 10, wherein light from the second waveguide is incident on an interface of the optical component at an angle that is greater than a critical angle for total internal reflection.

12. The optical probe according to claim 10, further comprising a reflective film on a surface of the optical component such that the light is reflected from the elliptical core of the second waveguide based upon total internal reflection.

13. The optical probe according to claim 10, wherein the optical component that reflects light from the second waveguide and through the sheath is a mirror.

14. The optical probe according to claim 1, wherein the waveguide has asymmetric optical powers and has a optical power of the sheath along a first axis which has the following relationship:

$$P_{fiber_x} \cong P_{fiber_y} + P_{sheath_y} - P_{fiber_y} P_{sheath_y} L$$

in which:
    $P_{fiber_y}$ is a first optical power of the waveguide;
    $P_{fiber_x}$ is a second optical power of the waveguide orthogonal to the first optical power;
    $P_{sheath_y}$ is the optical power of the sheath along the first axis; and
    L is an optical distance between the waveguide and the sheath.

15. An optical probe comprising:
    a first waveguide for guiding a light;
    a second waveguide for guiding a light with asymmetric optical power; and
    a sheath,
    wherein the first waveguide and second waveguide guide at least one light through the sheath, and
    wherein the second waveguide has asymmetric optical powers and has an optical power of the sheath along a first axis which has the following relationship:

$$P_{fiber_x} \cong P_{fiber_y} + P_{sheath_y} - P_{fiber_y} P_{sheath_y} L$$

in which:
    $P_{fiber_y}$ is a first optical power of the second waveguide;
    $P_{fiber_x}$ is a second optical power of the second waveguide orthogonal to the first optical power;
    $P_{sheath_y}$ is the optical power of the sheath along the first axis; and
    L is an optical distance between the second waveguide and the sheath.

16. The optical probe according to claim 15, wherein the second waveguide is selected from one of: a polarization maintaining fiber; a plastic optical fiber; a photonic crystal fiber; and a GRIN lens.

* * * * *